United States Patent
Wu et al.

(10) Patent No.: US 6,979,184 B2
(45) Date of Patent: Dec. 27, 2005

(54) MANUAL NEGATIVE PRESSURE PUMP DEVICE

(76) Inventors: An Chiuan Wu, 235 Chung-Ho Box 8-24, Taipei (TW); Shin Shian Huang, 235 Chung-Ho Box 8-24, Taipei (TW); Kuo Bau Wu, 235 Chung-Ho Box 8-24, Taipei (TW)

( * ) Notice: Subject to any disclaimer, the term of this patent is extended or adjusted under 35 U.S.C. 154(b) by 327 days.

(21) Appl. No.: 10/350,400

(22) Filed: Jan. 17, 2003

(65) Prior Publication Data

US 2004/0105769 A1 Jun. 3, 2004

(30) Foreign Application Priority Data

Nov. 29, 2002 (TW) ........................................ 91219401 U (51) Int. Cl.7 ............................ F04B 39/10; F04B 53/00
(52) U.S. Cl. .................... 417/555.1; 417/234; 417/552; 417/562; 417/569
(58) Field of Search ............................ 417/234, 555.1, 417/552, 562, 566, 569, 567

(56) References Cited

U.S. PATENT DOCUMENTS

| 514,900 | A | * | 2/1894 | Black | 417/552 |
|---|---|---|---|---|---|
| 3,131,646 | A | * | 5/1964 | Parrott | 417/454 |
| 5,478,216 | A | * | 12/1995 | Neward | 417/440 |
| 5,498,246 | A | * | 3/1996 | Deutchman et al. | 604/227 |
| 5,620,314 | A | * | 4/1997 | Worton | 417/550 |
| 5,655,890 | A | * | 8/1997 | Liao | 417/234 |

* cited by examiner

Primary Examiner—Cheryl J. Tyler
Assistant Examiner—Timothy P. Solak (57) ABSTRACT

A manual negative pressure pump device comprises a suction cylinder, a handle, a pull, a piston, and an expandable spring which forms a vacuum absorbing device. A front end of the suction cylinder is a thread post with outer thread. The thread post has a central through hole and a plurality of small air holes around the through hole. The thread post is screwed with a nut of a joint. A valve and a drain-proof ring are installed between the joint and the thread post. The valve is a rubber washer and two ends of the washer have respective pins. The two pins are inserted into a central through hole of the joint and the central through hole of the thread post. The central through holes of the joint and the thread post are retained with a predetermined distance.

4 Claims, 10 Drawing Sheets

MANUAL NEGATIVE PRESSURE PUMP DEVICE

FIELD OF THE INVENTION

The present invention relates to pumps, and particularly to a manual negative pressure pump device which can be used in many fields, and particularly to vacuum device used in medicine.

BACKGROUND OF THE INVENTION

Figure 1:
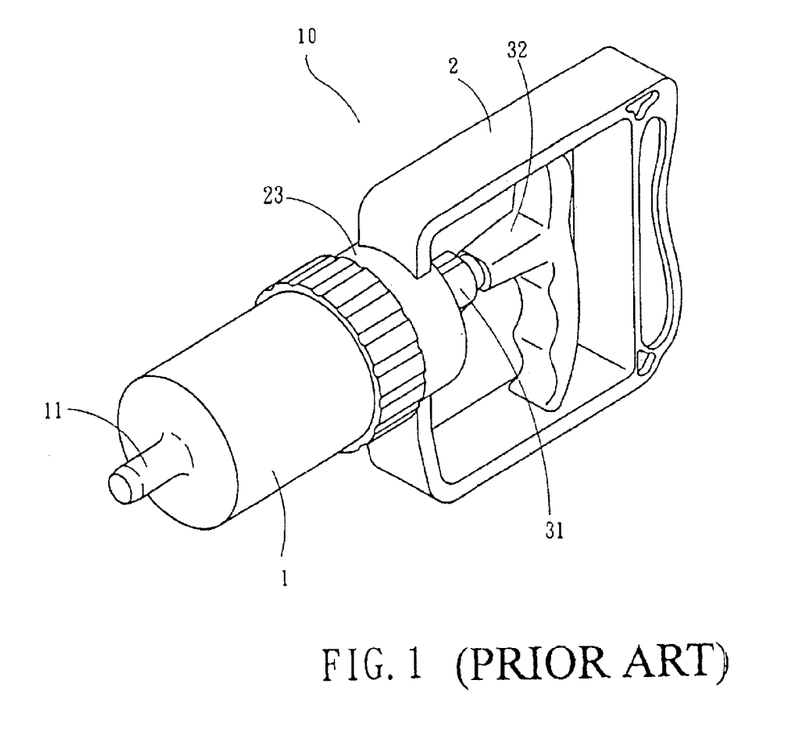
FIG. 1 is an assembled perspective view of the manual negative pressure pump device of the prior art.
Figure 2:
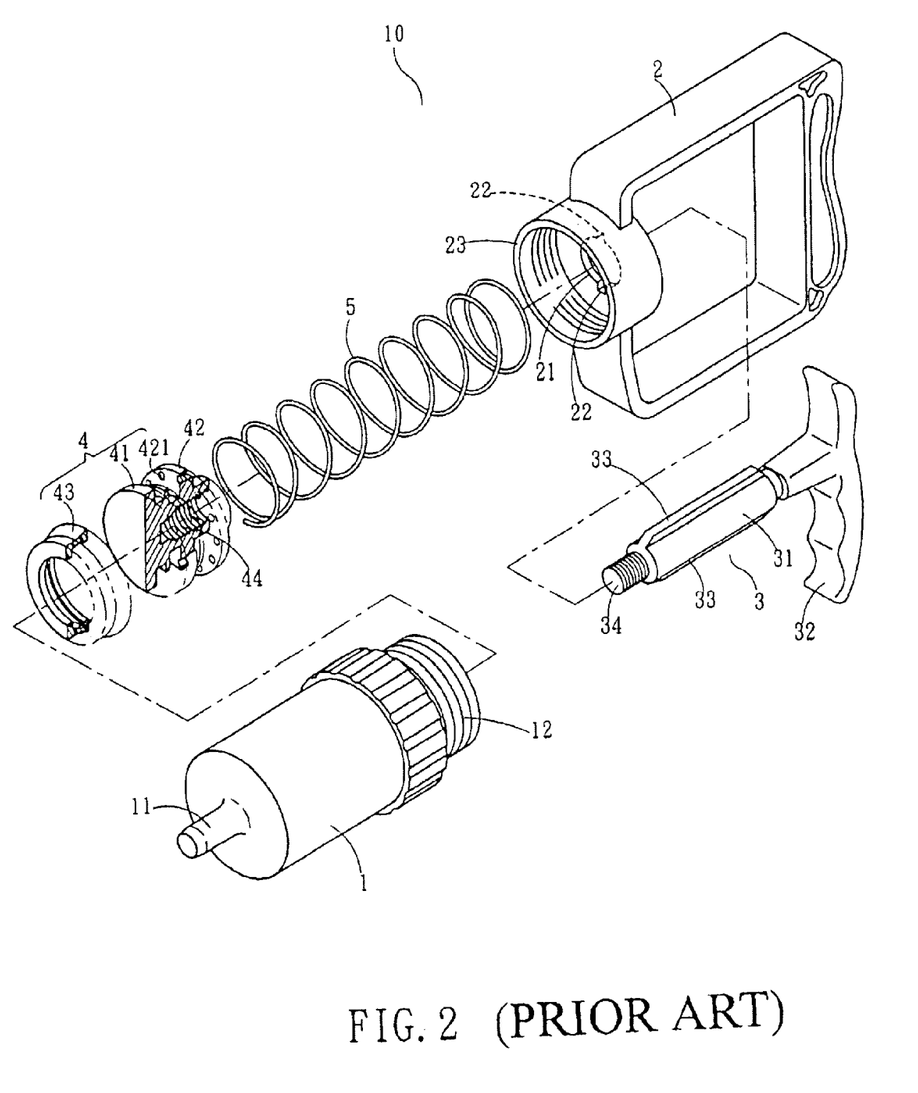
FIG. 2 is an exploded perspective view of the manual negative pressure pump device of the present invention.
Figure 3:
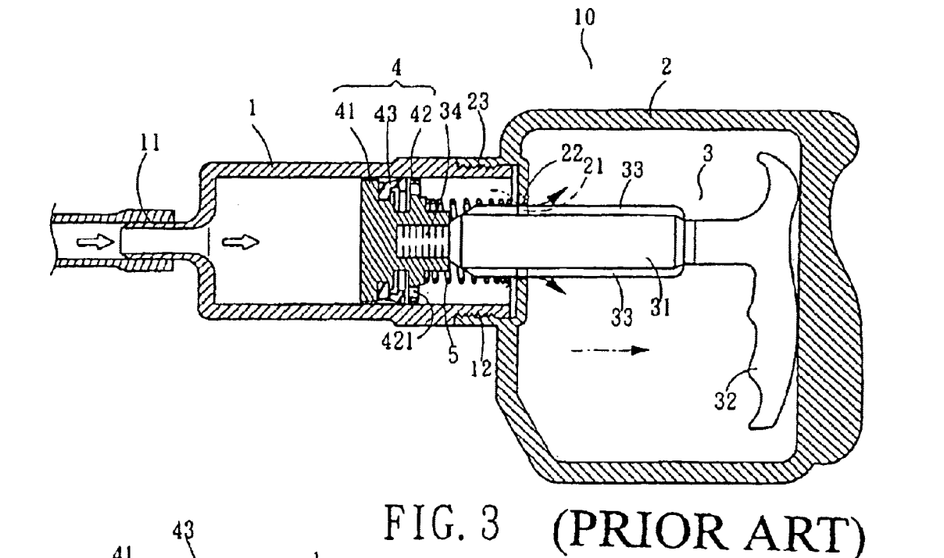
FIG. 3 is a schematic view showing the operation of the manual negative pressure pump device in the present invention.

Referring to FIGS. 1 and 3, the assembled perspective view and the exploded view of the conventional male stud 24 are illustrated. The prior art includes a suction cylinder 1 which is a long pump, a frame-like handle 2 connected to a rear end of the suction cylinder 1; and a pull 3 which is formed by a transversal pull rod 31 passing through the suction cylinder 1. A T shape pull handle 32 is connected to a rear end of the pull rod 31. A piston 4 is installed in the suction cylinder 1 and is fixed to a font end of the pull rod 31. An expandable spring 5 is serially connected to the pull rod 31 and a front end thereof resists against the piston 4 and a rear end thereof resists against the frame like handle.

A front end of the suction cylinder 1 is an air opening, and a rear end thereof is screwed into a female screw 23 by a male thread 12. An outer edge of the pull rod 31 of the pull 3 is installed with a plurality of protruded guides 33. The guides 33 of the pull 31 pass through the through hole 21 and guide recesses 22 of the handle 2. A front end of the pull rod 31 is firmly secured to the screw hole 44 of the piston 4 by a connected screw rod 34. The piston 4 is formed by an annular front guide 41, an annular rear guide 42 and a trapezoidal rubber absorbing disk 43. The rear guide 42 is annularly arranged with a plurality of small air holes 421. The rubber absorbing disk 43 is tightly matched to the inner wall of the suction cylinder 1.

Figures 4, 4A:
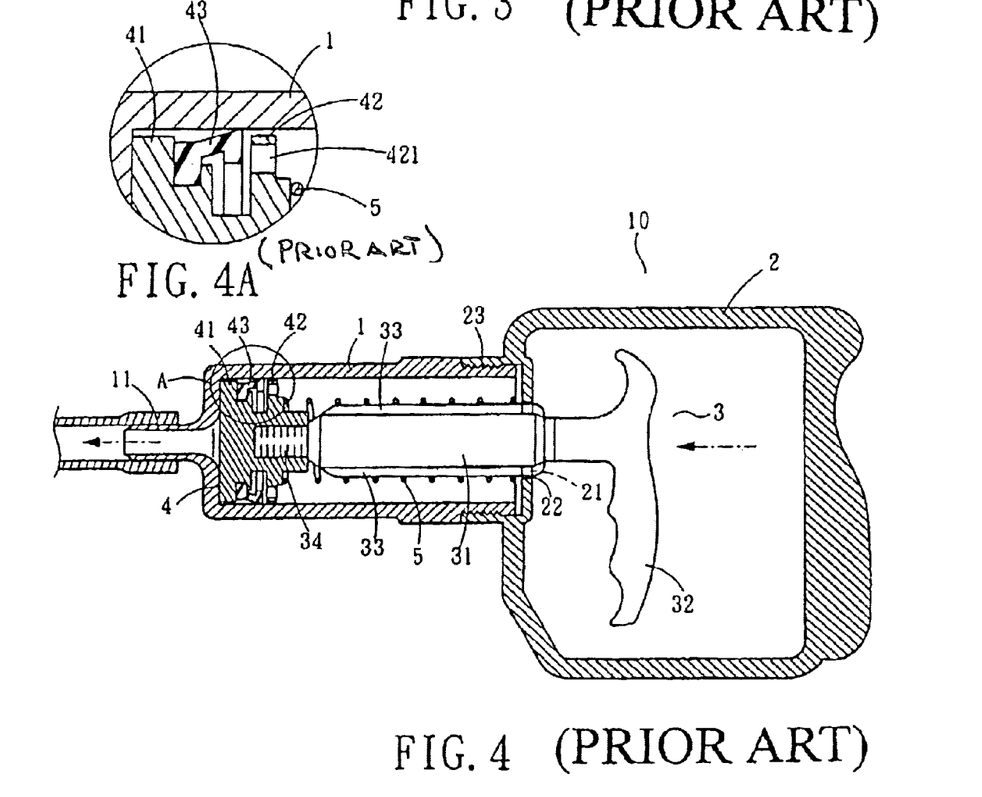
FIG. 4 is a schematic view showing another operation of the manual negative pressure pump device of the present invention.
FIG. 4A is an enlarged schematic view of the part A in FIG. 4.

Referring to FIGS. 3 and 4, when the suction cylinder 1 absorbs air, as shown in FIG. 3, the pull 3 will pull backwards so that the piston 4 moves backwards. Since the suction cylinder 1 will induce a negative pressure, air in the vacuum will be absorbed in the suction cylinder 1. The air originally in the suction cylinder 1 and after the piston 4 will be compressed when the piston 4 moves so that the air will be drained out from the through hole 21 and the guide recess 22. On the contrary, when the pull moves forwards, the piston 4 will move forwards. Then air in front of the piston 4 will be compressed so that air passes through the rubber absorbing disk 43 (referring to FIG. 4A) and the small air hole 21 of the rear guide 42 to flow backwards until the suction cylinder 1 absorbs air again, the air is compressed again as the piston move backwards to vent out from the through hole 21 and the guide recess 22.

The prior art has the following defects,

When the pull 3 and the piston 4 moves forwards at the same time, the air in the suction cylinder 1 will be pressed and then is sprayed out from the air opening 11 to enter into a vacuum device. Since the air opening 11 has no check valve, the air original suctioned by the suction cylinder 11 will reversely return to the vacuum device after being compressed by the piston 2.

The through hole 21 and the guide recesses 22 before the handle 2 can be inserted by the pull rod, moreover, it can be used as a rear exhausting opening of the suction cylinder 1. However, the thickness of the through hole 21 and the guide recesses 22 are too thin so that the movement of the pull rod 31 and the guide piece 33 are unsteady. When they move reciprocally around the pull rod 3, they will shift or be hindered.

A front end of the handle 2 is a female screw 23 and the rear end of the suction cylinder 1 has outer thread. When the two are combined, the outer thread is screwed into the female screw 23, but in general, the screw effect is not preferred and the screw operation is not smooth.

SUMMARY OF THE INVENTION

Accordingly, the primary object of the present invention is to provide a manual negative pressure pump device which comprises a suction cylinder, a handle, a pull, a piston, and an expandable spring which forms a vacuum absorbing device. A front end of the suction cylinder is a thread post with outer thread. The thread post has a central through hole and a plurality of small air holes around the through hole. The thread post is screwed with a nut of a joint. A valve and a drain-proof ring are installed between the joint and the thread post. The valve is a rubber washer and two ends of the washer have respective pins. The two pins are inserted into a central through hole of the joint and the central through hole of the thread post. The central through holes of the joint and the thread post are retained with a predetermined distance.

The various objects and advantages of the present invention will be more readily understood from the following detailed description when read in conjunction with the appended drawing.

BRIEF DESCRIPTION OF THE PREFERRED EMBODIMENTS

Figure 5:
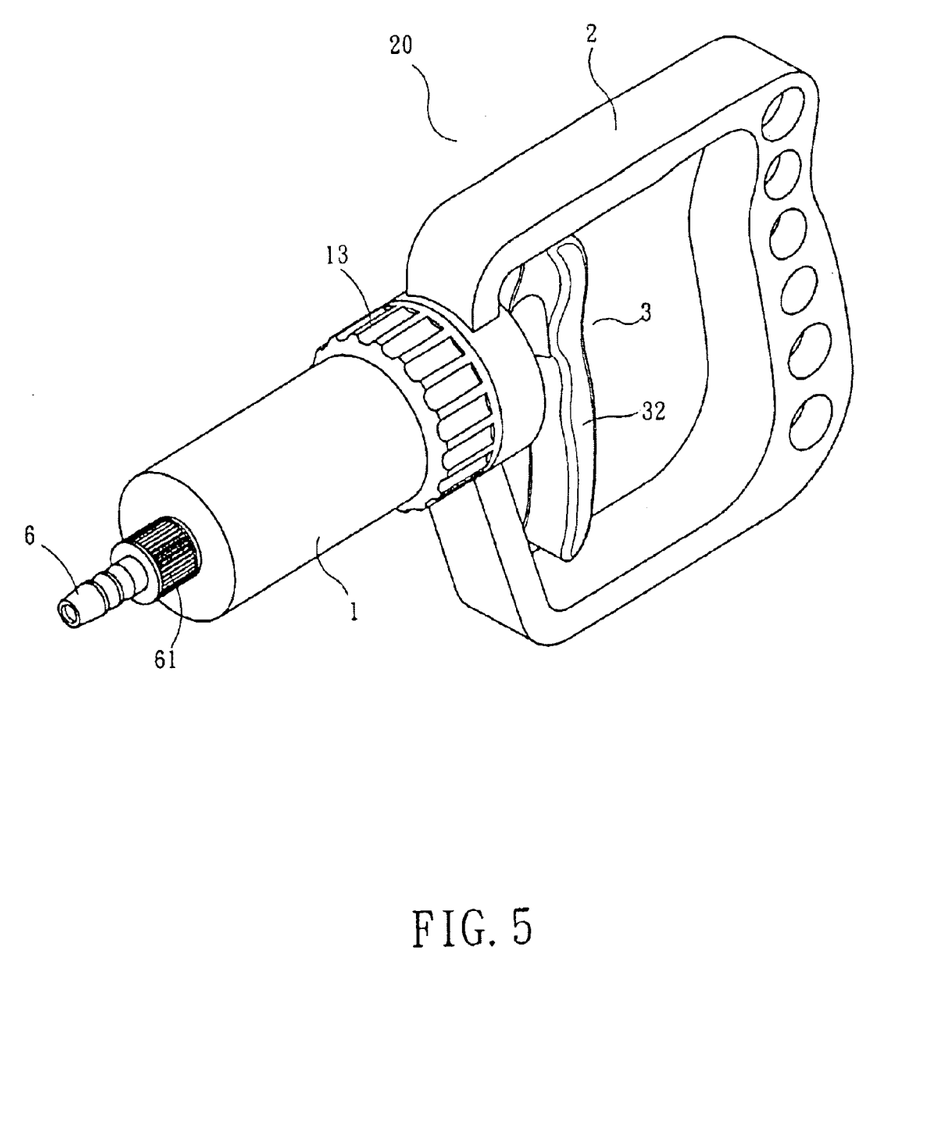
FIG. 5 is an assembled perspective view of the manual negative pressure pump device of the present invention.
Figure 6:
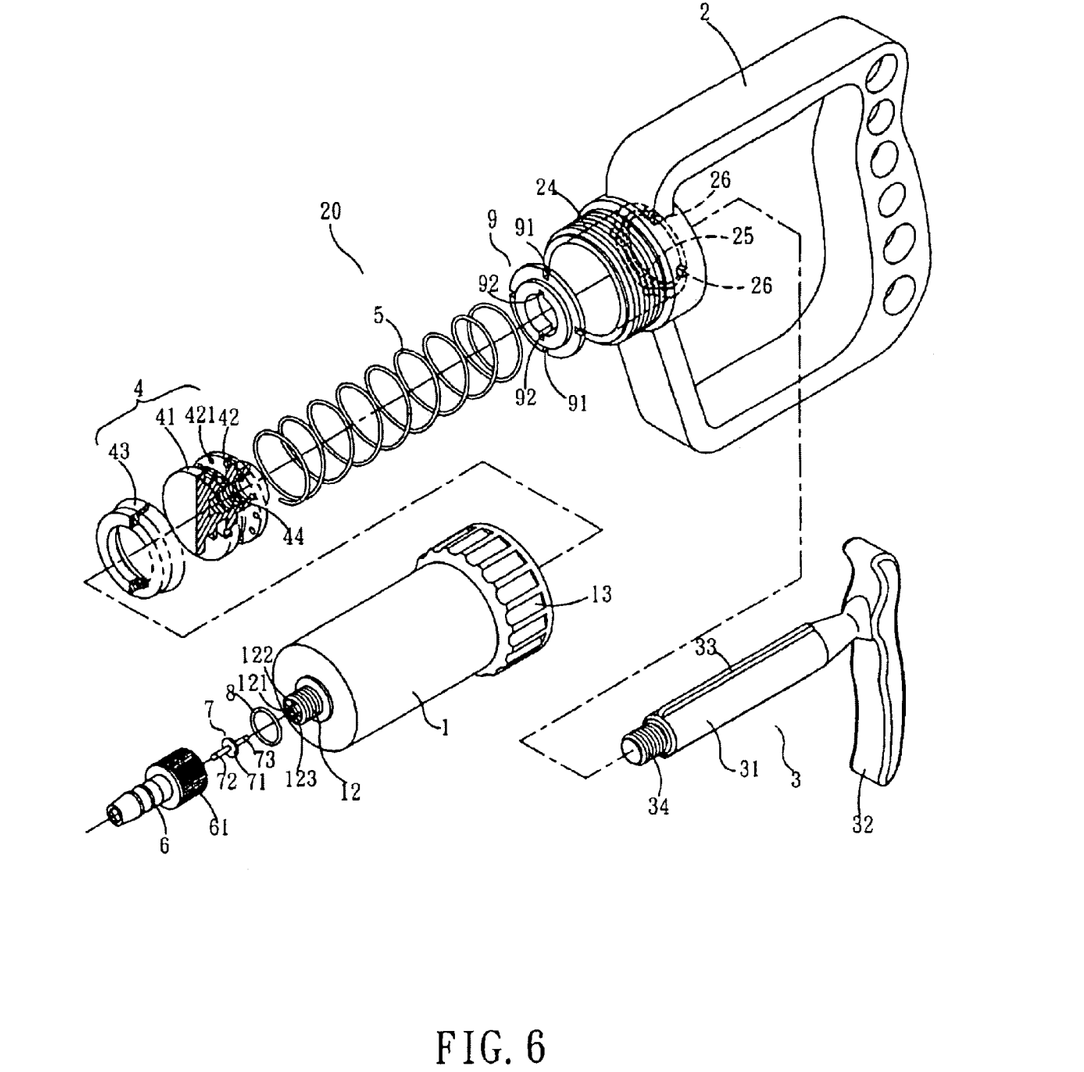
FIG. 6 is an exploded perspective view of the manual negative pressure pump device of the present invention.

Referring to FIGS. 5 and 6, the assembled perspective view and exploded view of the present invention are illustrated. The manual negative pressure pump device of the present invention has a structure like those used in the prior art. The manual negative pressure generating device includes a suction cylinder 1, a handle 2, a pull 3, a plug 4 and an extension spring 5.

A front end of the suction cylinder 1 has a thread post 12. The post 12 has a central hole 121 and a plurality of small air holes 122 are arranged around a periphery of the central hole 121. The thread post 12 can screw with the nut 61 of the joint 6. A valve 7 and a seal ring 8 are installed between the joint 6 and the post 12.

Moreover, the frame-like handle 2 has a male stud 24 which is screwed to a female mask 13 at a distal end of the suction cylinder 1. A front end of the handle 2 has a stepped through hole 25. An outer wall of the hole edge has a plurality of blocks 26. The through hole 25 is at an inner center of the male stud 24. Besides, a stepped buckle ring 9 is embedded to the through hole 25 (referring to FIG. 7). An outer edge of the buckle ring 9 has a plurality of recesses 91 which are spaced with an equal angle. The hole of the buckle ring 9 has a plurality of slots 92 for guiding a guide 33 protruded from the pull 3.

The valve 7 is a rubber washer 71 and two ends thereof have symmetric pins 72 and 73 which can be inserted into the through hole 62 of the joint 6 and the through hole 121 of the thread post 12 so that the assembly work can be performed easily. To have a better drain-proof effect, the through holes 62 and 121 are formed with protruding rings 63 and 123, respectively (referring to FIG. 7A) so as to have a preferred drain-proof effect. The two protruding rings 63 and 123 are retained with a predetermined distance. When the washer 71 is in contact with any one of the protruding rings 63 and 123, a better sealing effect is formed. If no protruding ring is formed, then washer 71 will surface-contact the outer wall of the central through holes. As a result, the drain-proof effect is deteriorated.

Figure 7:
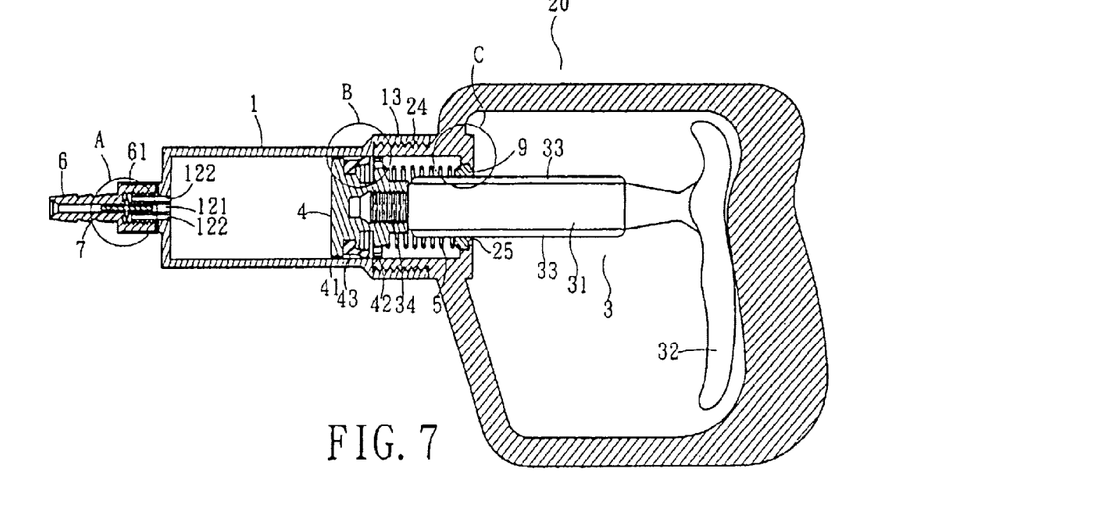
FIG. 7 is an operational schematic view of the manual negative pressure pump device of the present invention.
Figure 7A:
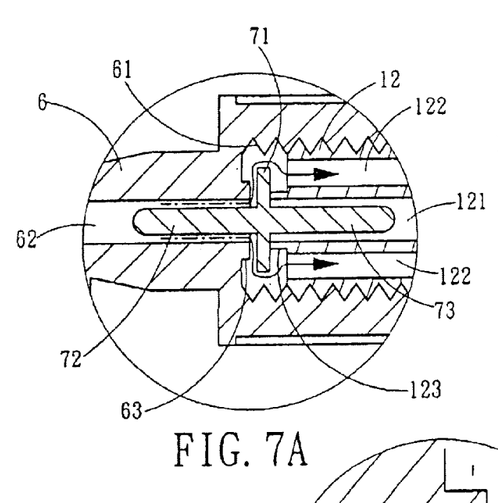
FIG. 7A is an enlarged schematic view of the valve in part A of FIG. 7.
Figure 7B:
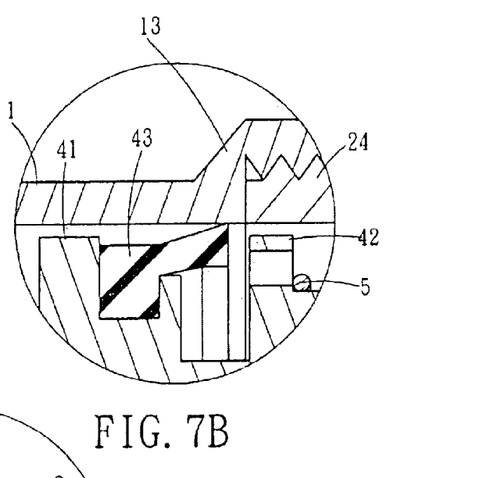
FIG. 7B is an enlarged schematic view of the piston in part B of FIG. 7.
Figure 7C:
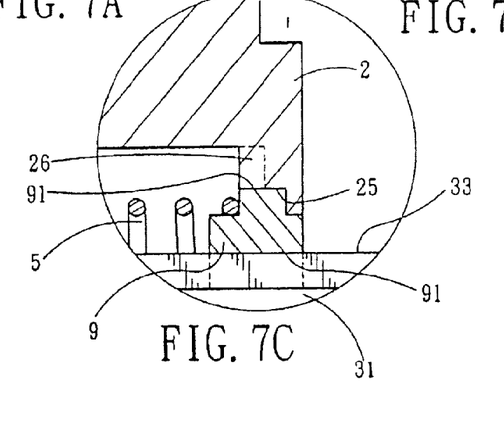
FIG. 7C is an enlarged schematic view showing the buckle ring of part C in FIG. 7.

Moreover, the thickness of the stepped buckle ring 9 is larger than thickness of the stepped through hole 25 (referring to FIG. 7C). Moreover, the contact area of the pull rod 31 and the guide 33 is enlarged. As a result, the movement of the pull 3 will not be hindered by the vibration or movement of the pull rod 31. The buckle ring 9 is pressed by the spring 5 and the recesses 91 are matched to the blocks 26 so that the abnormal movement of the buckling ring 9 will be prevented. Furthermore, the screwing of the female mask 13 and the male stud 24 of the handle 2 has a perfect effect. This is because the female mask 13 of the suction cylinder 1 is easier to be assembled to the male stud 24 of the handle 2. In rotation, it is only necessary to rotate the suction cylinder 1. It is unnecessary to rotate the handle 2 and thus the assemble work can be performed easily.

Figure 8:
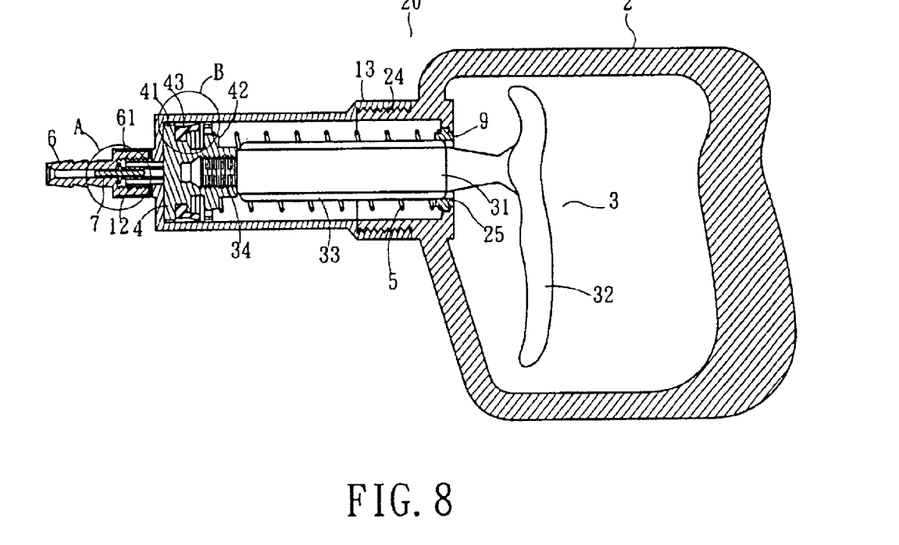
FIG. 8 is a schematic view showing the operation of the manual negative pressure pump device of the present invention.
Figure 8A:
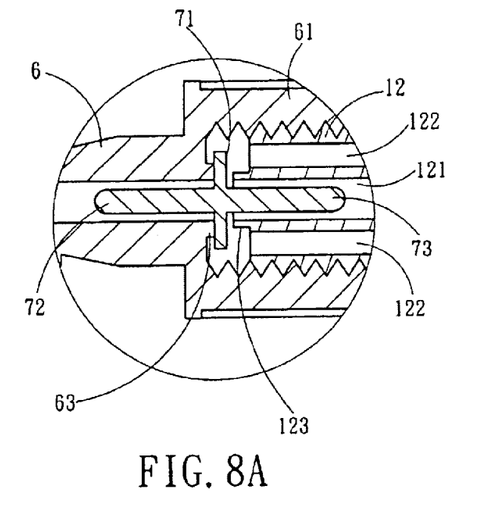
FIGS. 8A and 8B show the different operation states of the manual negative pressure pump device of the present invention.
Figure 8B:
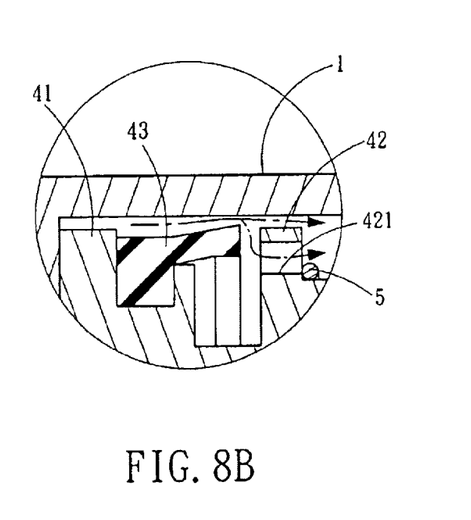

Referring to FIGS. 7 and 8, in FIG. 7, when the pull 3 moves backwards to drive the piston 4 to move, the suction cylinder 1 will has a negative pressure. Thus, air in the vacuum device will be absorbed into the suction cylinder 1. Then the valve 7 is absorbed by the suction cylinder 1 and the washer 71 is adhered to the protruding ring 23 so as to seal the central through hole 121. As a result, the central through hole 62 of the joint 6 is opened. Then air passes through the central through hole 62 and then into the small air holes 122. Then the air flows into the suction cylinder 1. The air original in the suction cylinder 1 and behind the piston 4 will move backwards by the action of the piston 4. Then the air is vented out from the through hole 21 and the guide recesses 22 at a rear end thereof. When the piston 4 moves, an outer edge of the rubber suction disk 43 will tightly adhere to an inner wall of the suction cylinder 1 (referring to FIG. 7B). With reference to FIG. 8, by the pull 3, the piston 4 moves forwards with the movement of the pull 3. At this time, air in the suction cylinder 1 and before the piston 4 is compressed to extrude forwards so that the valve 7 will cause the washer 71 to adhere to a front side of the protruding ring 63 by the venting effect (referring to FIG. 8A). Thereby, air can not flow into the central through hole 62 and thus can not flow into the vacuum device. Since air before the piston 4 can be not vented out, it only compresses the rubber suction disk 43 backwards (referring to FIG. 8B) so that the suction disk 43 is compressed and thus the diameter thereof is reduced.

Since air before the piston 4 can not be exhausted out, the air will flow backwards to compress the suction disk 43 and the small air holes 421 of tile rear guide 42 to flow backwards until the suction cylinder 1 suctions air again, In the process that the piston 4 moves backwards, the air is compressed and then vents out from the through hole 21 and the guide recesses 22 at the rear end. Because in the present invention, after the joint 6 is added, when the piston 4 in the suction cylinder 1 returns, air will not flow into the vacuum device along a reverse direction.

Figure 9:
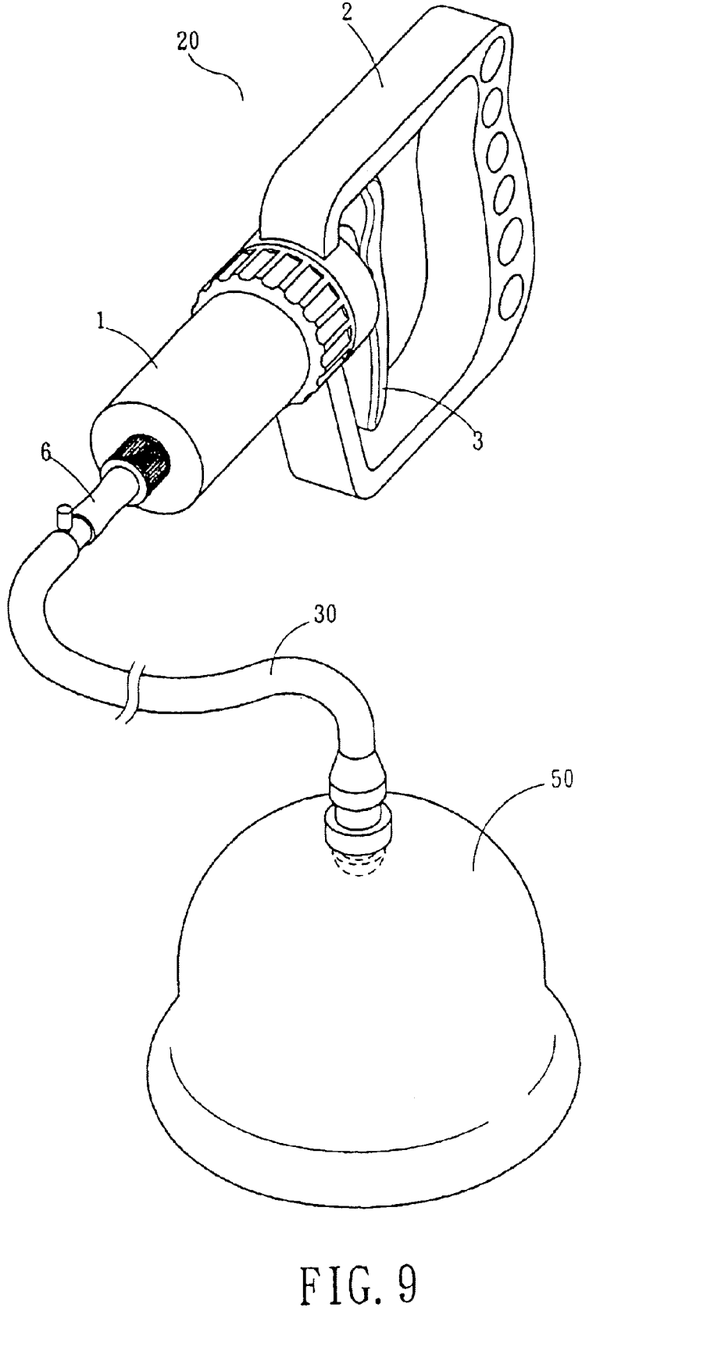
FIG. 9 shows that the present invention is used with a cup of a breast exercising device.
Figure 10:
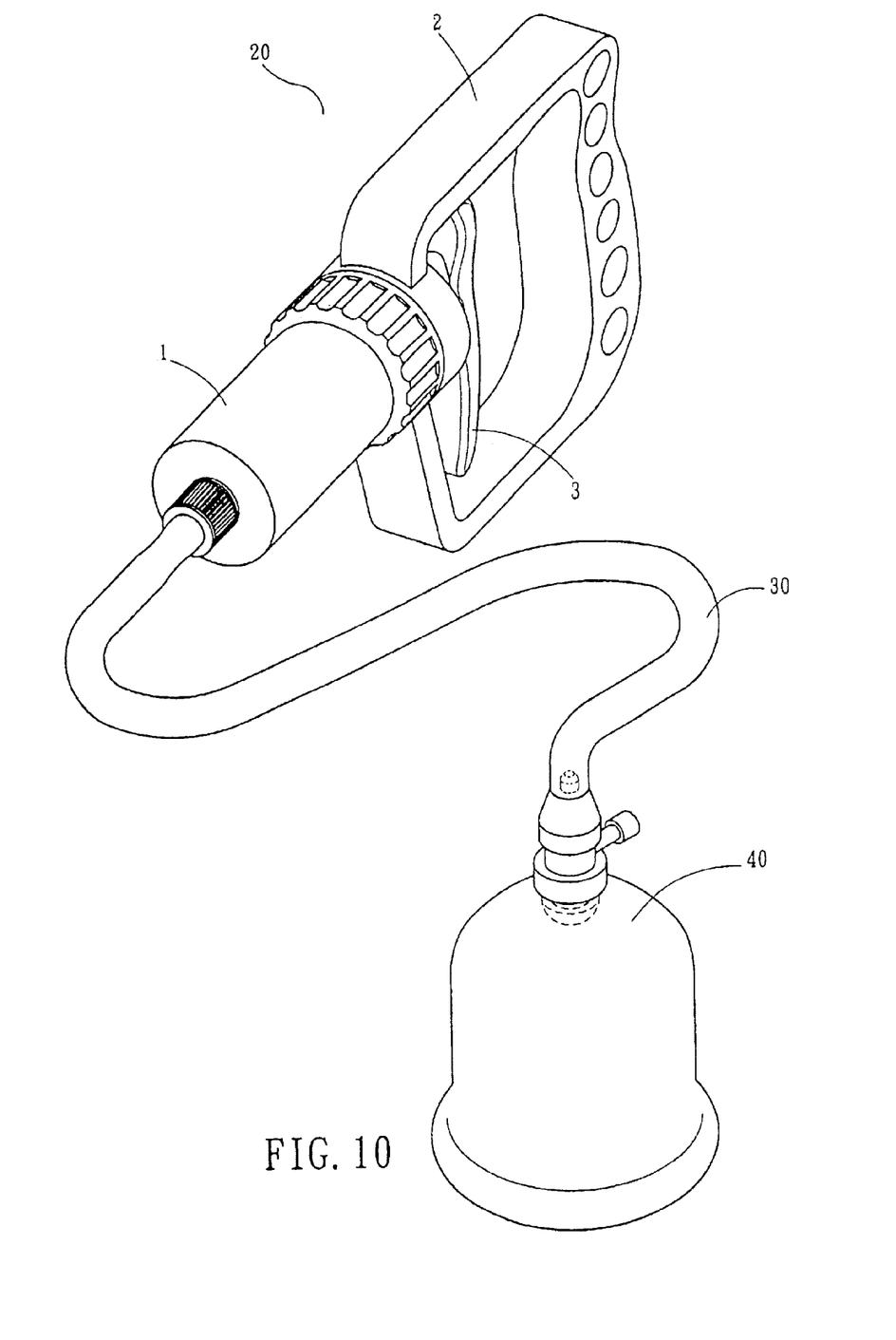
FIG. 10 shows that the present invention is used with a can used in Chinese medicine.
Figure 11:
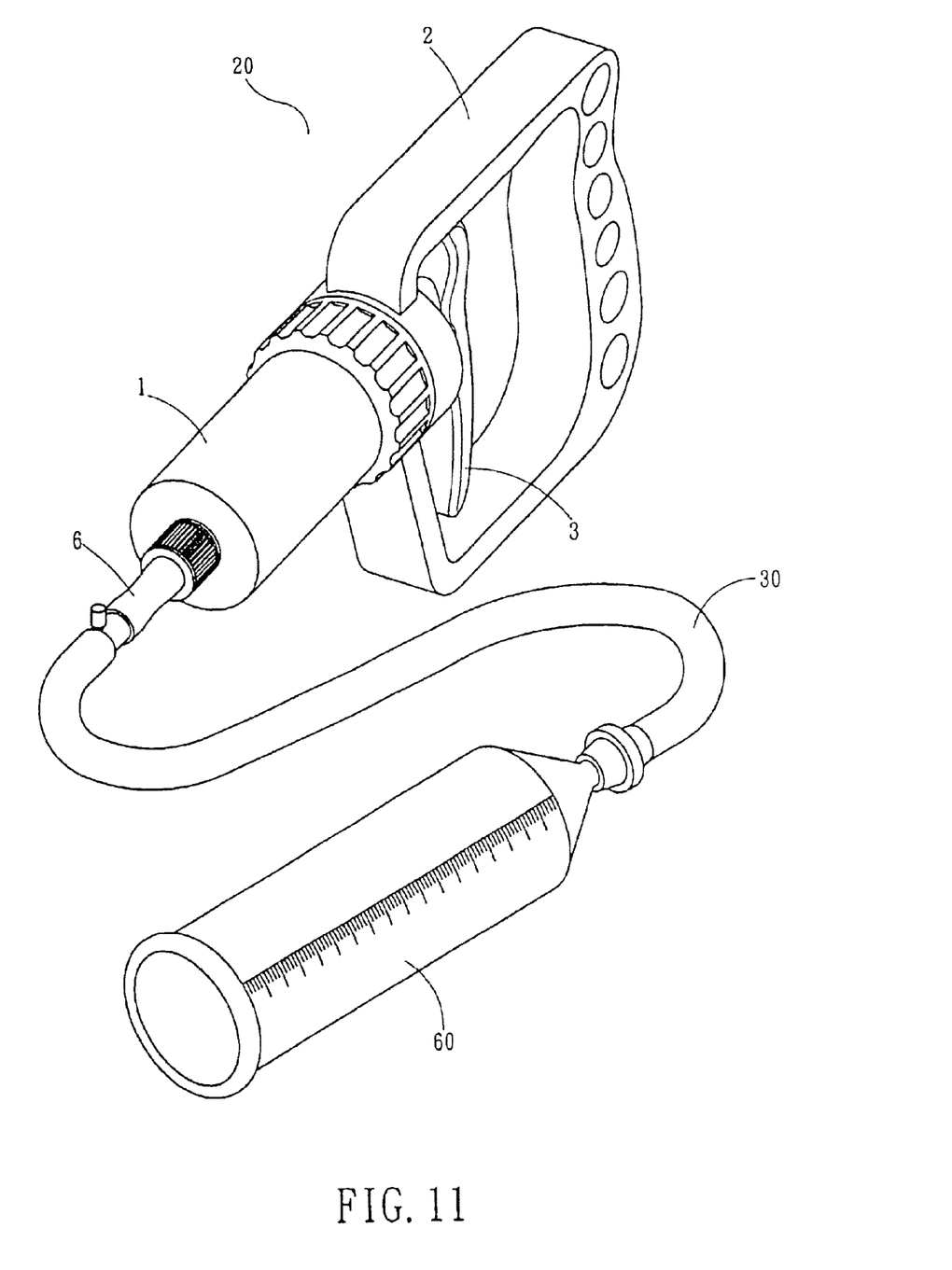
FIG. 11 shows that the present invention is used with a cup of an absorbing cylinder to promote the erection of man.

With reference to FIGS. 10 and 11, the applications of the manual negative pressure pump device 20 and the connecting tube 30 are illustrated. FIG. 9 shows that the present invention is used with a cup 50 of a breast exercising device. FIG. 10 shows that the present invention is used with a can 40 used in Chinese medicine. FIG. 11 shows that the present invention is used with a cup of an absorbing cylinder 60 to promote the erection of man.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A manual negative pressure pump device comprising:

a suction cylinder being a long pumping cylinder;

a handle connected to a rear end of the suction cylinder;

a pull being a rod transversally inserted into the suction cylinder; a rear end of the pull being connected to a pull rod which is out of the suction cylinder;

a piston installed in the suction cylinder and being fixed at a front end of the pull rod; and an expandable spring surrounding the pull rod and a front end of the expandable spring resisting against a piston and a rear end thereof resisting a handle;

wherein by above components, a vacuum absorbing device is formed; characterized in that:

a front end of the suction cylinder is a thread post with outer thread; the thread post central through hole and a plurality of small air holes around the through hole; the thread post is screwed with a nut of a joint; a valve and a drain-proof ring are installed between the joint and the thread post; the valve is a rubber washer and two end of the washer have respective pins; the two pins are inserted into a central through hole of the joint and the central through hole of the thread post; the central through holes of the joint and the thread post are retained with a predetermined distance.

2. The manual negative pressure pump device as claimed in claim 1, wherein a front end of the handle has a stepped through hole; an outer wall of an edge of the stepped through hole has a plurality of blocks spaced with a predetermined distance; a stepped buckle ring is embedded to the stepped through hole; an outer edge of the stepped buckle ring has a plurality of recesses which are corresponding to the blocks; a hole of the stepped buckle ring has a plurality of slots for guiding a guide protruded from the pull.

3. The manual negative pressure pump device as claimed in claim 1, wherein central through holes of the thread post and the joint are installed with respective protruded rings; the two protruded rings are spaced with a predetermined distance for matching the configuration of the valve.

4. The manual negative pressure pump device as claimed in claim 1, wherein a front end of the handle has a male nut and a distal end of the suction cylinder is a female mask; the female mask is screwed to the male nut.

* * * * *